United States Patent [19]

Denis

[11] Patent Number: 5,179,231

[45] Date of Patent: Jan. 12, 1993

[54] PREPARATION OF HEXENE-1,6-DIOIC ACIDS

[75] Inventor: Philippe Denis, Decines, France

[73] Assignee: Rhone-Poulenc Chimie, Courbevoie, France

[21] Appl. No.: 626,774

[22] Filed: Dec. 13, 1990

[30] Foreign Application Priority Data

Dec. 13, 1989 [FR] France ................. 89 16755

[51] Int. Cl.$^5$ .................... C07C 51/12; C07C 273/00
[52] U.S. Cl. ..................... 562/519; 564/47; 564/56; 564/58; 564/102; 564/183; 564/184; 564/187; 564/192
[58] Field of Search ......................... 562/519

[56] References Cited

FOREIGN PATENT DOCUMENTS 0124160 7/1984 European Pat. Off. .
89/06019 2/1990 France .

*Primary Examiner*—Jose G. Dees
*Assistant Examiner*—Keith MacMillan
*Attorney, Agent, or Firm*—Burns, Doane, Swecker & Mathis

[57] ABSTRACT

Hexene-1,6-dioic acids, e.g., hex-3-ene-1,6-dioic acid, are prepared by reacting carbon monoxide with at least one butenediol, in a polar, aprotic, basic solvent, in the presence of a catalytically effective amount of palladium values and at least one inorganic halide, the cation of which halide being an alkali or alkaline earth metal and the anion thereof being a chloride or bromide.

13 Claims, No Drawings

PREPARATION OF HEXENE-1,6-DIOIC ACIDS

CROSS-REFERENCE TO COMPANION APPLICATIONS

Copending applications Ser. No. 07/627,007 filed Dec. 13, 1990 and Ser. No. 07/626,833, filed Dec. 13, 1990, both filed concurrently herewith and both assigned to the assignee hereof.

BACKGROUND OF THE INVENTION

1. Field of the Invention

The present invention relates to an improved process for the preparation of hexene-1,6-dioic acids, and, in particular, hex-3-ene-1,6-dioic acid. Hex-3-ene-1,6-dioic acid is a valuable intermediate that can facilely be hydrogenerated into adipic acid.

2. Description of the Prior Art

Adipic acid, one of the starting materials for the production of nylon 66, is currently produced in vast amounts per annum. By reason of this fact alone, any new route for the synthesis of this diacid and/or derivatives thereof would be of fundamental interest to this art.

Published French Patent Application No. 89/06,019 describes a process for the preparation of such diacids by contacting but-2-ene-1,4-diol with carbon monoxide in the presence of a palladium-based catalyst, at elevated temperature and under a pressure higher than atmospheric pressure, and wherein the reaction is also carried out in the presence of at least one quaternary onium chloride of a Group VB element of the Periodic Table selected from nitrogen and phosphorus, such element being tetracoordinated to carbon atoms, with the proviso that the nitrogen may be coordinated to two pentavalent phosphorus atoms.

This reaction can be carried out in N-methylpyrrolid-2-one.

The process of the '019 application, which provides appreciable results both in respect of its activity and in respect of its selectivity for a straight-chain dicarbonylated compound, however, presents the disadvantage of requiring the presence of at least one quaternary onium halide as indicated above. These onium compounds are promoters which are relatively expensive or not readily available and are susceptible to degradation during prolonged use.

Thus, need exists in this art for an alternate process that does not require a halogenated organic promoter, and particularly one wherein all or part of such organic promoter may be replaced by an inorganic halogenated promoter which is more readily available and relatively more stable over prolonged use.

SUMMARY OF THE INVENTION

Accordingly, a major object of the present invention is the provision of an improved process for the preparation of hexene-1,6-dioic acids, notably hex-3-ene-1,6-dioic acid, by reacting carbon monoxide with at least one butenediol in the presence of a palladium-based catalyst and a halide, such reaction being carried out in a polar, aprotic, basic solvent and said halide comprising at least one inorganic halide, the cation of which is an alkali metal or an alkaline earth metal cation and the anion of which is a chloride or bromide.

DETAILED DESCRIPTION OF THE PREFERRED EMBODIMENTS OF THE INVENTION

More particularly according to the present invention, by "butenediol" is intended but-2-ene-1,4-diol, but-1-ene-3,4-diol or mixtures thereof.

Indeed, it has now surprisingly been found that the process of the invention permits the subject dicarbonylation to be carried out under conditions of pressure and temperature which are acceptable on an industrial scale, with an appreciable selectivity for straight-chain dicarbonylated compounds, the proportions of monocarbonylated compounds and branched dicarbonylated compounds being minimal.

The process according to the present invention is carried out in the presence of a palladium-based catalyst.

While the precise nature of the mechanism of such catalysis is not totally understood, it has been found that a very wide variety of palladium compounds and metallic palladium are useful catalysts, or precursors thereof, for carrying out the process of the present invention.

Exemplary sources of palladium which may thus be used include the following:

(i) metallic palladium, if appropriate deposited onto a support therefor, such as charcoal, alumina or silica;

(ii) $PdCl_2$, $Pd(OAc)_2$;

(iii) the salts or $\pi$-allyl complexes of palladium, in which the anion coordinated to the Pd cation is selected from among the following anions:

carboxylates, such as formate, acetate, propionate or benzoate; acetylacetonate and halides such as $Cl^-$ and $Br^-$, and preferably $Cl^-$.

Advantageously, palladium chloride is used.

The precise amount of catalyst to be used, which may vary over wide limits, will primarily depend on a compromise between the desired efficiency and the consumption of catalyst and the other reaction conditions. In general, good results are obtained using a palladium concentration in the reaction mixture ranging from $10^{-3}$ to 1 mol/l. Preferably, this concentration ranges from $2 \cdot 10^{-3}$ to $5 \cdot 10^{-2}$ mol/l.

One of the essential characteristics of the process of the present invention is that the reaction is carried out in the presence of a polar, aprotic and basic solvent.

By "polar, aprotic and basic solvent" are especially intended compounds of the formula (I):

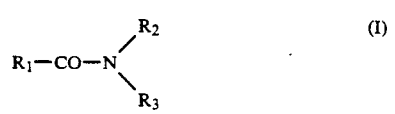

in which $R_1$, $R_2$ and $R_3$, which may be identical or different, are each an alkyl radical, a cycloalkyl radical, an aralkyl radical or a monocyclic aryl radical having up to 10 carbon atoms, with the proviso that two of the radicals $R_1$, $R_2$ or $R_3$ may together form a single divalent radical $-(CH_2)_y-$, in which y is an integer ranging from 3 to 12, and further wherein $R_1$ may be a radical of the formula (II):

(II)

in which $R_4$ and $R_5$, which may be identical or different, are each an alkyl radical having up to 4 carbon atoms.

Exemplary such solvents include tetramethylurea, N,N-dimethylacetamide, N,N-diethylacetamide, N,N-dicyclohexylacetamide, N,N-dimethylpropionamide, N,N-diethylpropionamide, N,N-diethyl-n-butyramide, N,N-dimethylbenzamide, N,N-dicyclohexylbenzamide, N,N-diethyl-m-toluamide, N-acetylpyrrolidine, N-acetylpiperidine, N-(n-butyryl)piperidine, N-methylpyrrolid-2-one, N-ethylpyrrolid-2-one, N-methylpiperid-2-one, N-methyl-epsilon-caprolactam.

N-Methylpyrrolid-2-one is particularly suitable for carrying out the subject process.

In general, the amount of solvent of such type constitutes at least 10% by volume of the reaction mixture; good results are obtained when it is used in an amount on the order of 20% to 85% by volume.

Of course, a mixture of such solvents may be used, as well as mixtures of at least one such solvent and a solvent which is inert under the reaction conditions but which does not fall within the above definition, such as a ketone, a saturated aliphatic hydrocarbon, or an aromatic hydrocarbon.

It is likewise possible to add an alkanol to the reaction mixture and thus to obtain, in whole or in part, the acids in question in the form of their corresponding diesters.

Another essential characteristic of the process according to the invention is that the reaction is also carried out in the presence of a halide, the cation of which is selected from among the alkali metal cations and the alkaline earth metal cations, the halide anion being selected from the chloride and bromide.

In a preferred embodiment of the invention, an alkali metal chloride or an alkaline earth metal chloride is used.

It has also been determined that the beneficial effect provided by the presence of an alkali metal chloride or bromide or alkaline earth metal chloride or bromide in the carbonylation mixture is perceptible from a molar ration $Cl^-$ (or $Br^-$)/palladium of 0.5; in particular, particularly desirable results are obtained when said ratio ranges from 1 to 50, a higher ratio, however, not being detrimental to the reaction.

Of course, a mixture of such inorganic halides or a mixture thereof with at least one quaternary onium halide as defined above can also be used according to the present invention.

The reaction is advantageously carried out in liquid phase at a temperature ranging from 50° to 150° C., preferably from 80° to 130° C., under a carbon monoxide pressure ranging from 20 to 250 bar, preferably from 90 to 180 bar.

Inert gases, such as nitrogen, argon or carbon dioxide, may also be present together with the carbon monoxide.

Upon completion of the reaction or at the end of predetermined reaction time, the desired diacid is recovered by any appropriate means, for example by extraction.

In order to further illustrate the present invention and the advantages thereof, the following specific examples are given, it being understood that same are intended only as illustrative and in nowise limitative.

In said examples to follow, the yields are expressed relative to the butenediol charged.

EXAMPLES 1 TO 6; Control Experiment (a):

The following reagents were introduced into a 125 cm³ stainless steel (Hastelloy B2) autoclave previously purged with argon:

(i) 4.4 g (50 mmol) of but-2-ene-1,4-diol;
(ii) 1 mat-g of palladium in the form of pdCl₂;
(iii) if necessary, 17 mmol of calcium chloride (magnesium chloride or alkali metal chloride); and
(vi) 25 cc of N-methylpyrrolid-2-one (NMP).

The autoclave was hermetically sealed, placed in a stirred furnace and connected to the pressurized gas feed. The reactor was purged cold with carbon monoxide and adjusted to 100° C. The pressure was then adjusted to 120 bar. When the absorption of carbon monoxide had ceased, the autoclave was cooled and degassed.

The reaction mixture was then esterified using methanol and then analyzed by gas phase chromatography.

The particular conditions and the results obtained are reported in Table I below, in which t(min) represents the absorption time and HD(%) represents the number of moles of hex-3-ene dioic acid formed per 100 moles of but-2-ene-1,4-diol charged.

The degree of conversion of the but-2-ene-1,4-diol was on the order of 100% in all of the experiments.

TABLE I

| Example | Nature of the halide | t (min) | HD (%) |
|---------|----------------------|---------|--------|
| a | none | 60 | 38 |
| 1 | LiCl | 60 | 71 |
| 2 | KCl | 60 | 45 |
| 3 | NaCl | 60 | 44 |
| 4 | CsCl | 60 | 44 |
| 5 | MgCl₂.6H₂O | 40 | 75 |
| 6 | CaCl₂ | 60 | 90 |

EXAMPLE 7

The procedure of Example 1 was repeated, but replacing NMP by an identical volume of dimethylacetamide.

The absorption time was 90 min; HD (%)=78.

EXAMPLE 8

The procedure of Example 1 was repeated, but replacing LiCl by a mixture of 8.5 mmol of tetrabutylphosphonium chloride and 8.5 mmol of LiCl.

The absorption time was 40 min; HD (%)=81.

EXAMPLES 9 to 11; Control Experiment(b):

A series of experiments was carried out using an operating procedure the same as that described above, using a charge containing;

(i) 25 cc of solvent or mixture of solvents;
(ii) 4.4. g (50 mmol) of but-2-ene-1,4-diol;
(iii) 17 mmol of LiCl; and
(vi) 1 mat-g of palladium in the form of PdCl₂.

The temperature was 100° C.; the pressure was controlled at 120 bar.

The particular conditions and the results obtained are reported in Table II below, in which the conventions used are the same as those of Table I.

TABLE II

| Example | NMP (cc) | Co-solvent nature | Co-solvent (cc) | t (min) | HD (%) |
|---|---|---|---|---|---|
| b | 0 | methyl isobutyl ketone | 25 | 75 | 0 |
| 9 | 5 | methyl isobutyl ketone | 20 | 70 | 34 |
| 10 | 12.5 | methyl isobutyl ketone | 12.5 | 90 | 73 |
| 11 | 12.5 | toluene | 12.5 | 60 | 72 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a hexene-1,6dioic acid, which comprises reacting carbon monoxide with at least one butenediol, in a polar, aprotic, basic solvent, in the presence of a catalytically effective amount of palladium values and at least one inorganic halide, the cation of which halide comprising an alkali or alkaline earth metal, and the anion thereof comprising a chloride or bromide.

2. The process as defined by claim 1, said solvent comprising a compound of the formula (I):

$$R_1-CO-N\begin{matrix}R_2\\R_3\end{matrix} \quad (I)$$

in which $R_1$, $R_2$ and $R_3$, which may be identical or different, are each an alkyl radical, a cycloalkyl radical, an aralkyl radical or a monocyclic aryl radical having up to 10 carbon atoms, with the proviso that two of the radicals $R_1$, $R_2$ or $R_3$ may together form a single divalent radical —$(CH_2)_y$—, wherein y is an integer ranging from 3 to 12, and further wherein $R_1$ may be a radical of the formula (II):

$$-N\begin{matrix}R_4\\R_5\end{matrix} \quad (II)$$

in which $R_4$ and $R_5$, which may be identical or different, are each an alkyl radical having up to 4 carbon atoms.

3. The process as defined by claim 1, wherein said solvent comprises at least 10% by volume of the reaction mixture.

4. The process as defined by claim 1, said solvent comprising N-methylpyrrolid-2-one.

5. The process as defined by claim 1, said inorganic halide comprising a chloride.

6. The process as defined by claim 1, wherein the molar ratio of the chloride or bromide anion to palladium ranges from 1 to 50.

7. The process as defined by claim 1, wherein the amount of palladium in the reaction mixture ranges from $10^{-3}$ to 1 mol/l.

8. The process as defined by claim 1, carried out at a reaction temperature ranging from 50° to 150° C.

9. The process as defined by claim 8, carried out at a pressure ranging from 20 to 250 bar.

10. The process as defined by claim 1, said butenediol comprising but-2-ene-1,4-diol, but-1-ene-3,4-diol or mixture thereof.

11. The process as defined by claim 1, said palladium values comprising palladium chloride.

12. The process as defined by claim 8, carried out at a temperature ranging from 80° to 130° C.

13. The process as defined by claim 9, carried out at a pressure ranging from 90 to 180 bar.

* * * * *